United States Patent [19]

Ferrera et al.

[11] Patent Number: 5,390,677
[45] Date of Patent: Feb. 21, 1995

[54] METHOD FOR ASSESSING AND DISPLAYING THE TRUE THREE DIMENSIONAL MAGNITUDE OF BLOOD VELOCITY

[75] Inventors: Katherine W. Ferrera, New York, N.Y.; V. Ralph Algazi, Davis, Calif.

[73] Assignee: The Regents of The University of California, Oakland, Calif.

[21] Appl. No.: 251,710

[22] Filed: May 31, 1994

[51] Int. Cl.$^6$ .............................................. A61B 8/06
[52] U.S. Cl. ............................ 128/661.09; 73/861.25
[58] Field of Search ...................... 128/660.01, 660.05, 128/661.08–661.10; 73/861.25

[56] References Cited

U.S. PATENT DOCUMENTS

| | | | |
|---|---|---|---|
| 3,771,355 | 11/1973 | Sachs | 128/660.07 |
| 4,062,237 | 12/1977 | Fox | 128/661.1 X |
| 4,074,564 | 2/1978 | Anderson | 73/596 |
| 4,257,278 | 3/1981 | Papadofrangakis et al. | 128/661.1 X |
| 4,265,126 | 5/1981 | Papadofrangakis et al. | 73/861.25 |
| 4,276,885 | 7/1981 | Tickner et al. | 128/662.02 |
| 4,431,936 | 2/1984 | Fu et al. | 310/335 |
| 4,519,260 | 5/1985 | Fu et al. | 73/861.25 |
| 4,530,363 | 7/1985 | Brisken | 73/861.25 X |
| 4,542,744 | 9/1985 | Barnes et al. | 73/602 |
| 4,580,574 | 4/1986 | Gavish | 128/774 X |
| 4,759,375 | 7/1988 | Namekawa | 73/861.25 X |
| 4,790,322 | 12/1988 | Iinuma | 128/661.1 |
| 4,790,323 | 12/1988 | Leavitt et al. | 128/661.09 |
| 4,807,636 | 2/1989 | Skidmore et al. | 128/661.1 |
| 4,913,159 | 4/1990 | Gardin et al. | 73/861.25 X |
| 4,932,415 | 6/1990 | Angelsen et al. | 128/661.09 |
| 5,000,184 | 3/1991 | Bonnefous | 128/661.09 |
| 5,062,430 | 11/1991 | Bonnefous | 128/661.09 |
| 5,109,856 | 5/1992 | Bonnefous et al. | 128/660.01 |
| 5,109,857 | 5/1992 | Roundhill et al. | 128/661.08 |
| 5,201,313 | 4/1993 | Katakura | 128/661.09 |
| 5,233,994 | 8/1993 | Shmulewitz | 128/661.08 |
| 5,243,988 | 9/1993 | Sieben et al. | 128/662.06 |
| 5,280,787 | 1/1994 | Wilson et al. | 128/660.05 X |
| 5,329,929 | 7/1994 | Sato et al. | 128/661.09 |

OTHER PUBLICATIONS

Sollish (1977) Ultrason. Tissue Charac. Linzer, ed. pp. 53–56.
Chivers et al. (1973) 2nd World Cong. Ultrasonics Med. 300–303.

Primary Examiner—Francis Jaworski
Attorney, Agent, or Firm—John P. O'Banion

[57] ABSTRACT

A method for assessing and displaying the true three dimensional magnitude of fluid velocity using ultrasonic imaging signals is disclosed. Fluid, such as blood, flowing through a vessel is subjected to ultrasound imaging signals using a transducer. Axial velocity of fluid motion in relation to the transducer beam is then determined from the imaging signals. Next, a region of laminar flow is identified using the axial velocity. Lateral transit time in the region of laminar flow is then estimated as an indication of velocity in the direction perpendicular to the transducer beam. The three dimensional velocity magnitude is then estimated using the lateral transit time and the total distance across the lateral beam width, or by using the beam to vessel angle which is estimated using the lateral transit time. The estimated three dimensional velocity is then displayed as a numerical representation or as an image as a two dimensional waveform as a function of time or as a color flow map where the velocity magnitude is represented by different colors and/or intensity of color.

27 Claims, 3 Drawing Sheets

METHOD FOR ASSESSING AND DISPLAYING THE TRUE THREE DIMENSIONAL MAGNITUDE OF BLOOD VELOCITY

This invention was made with Government support under Grant No. BCS-9108940, awarded by the National Science Foundation. The Government has certain rights in this invention.

BACKGROUND OF THE INVENTION

1. Field of the Invention

This invention pertains generally to ultrasonic diagnostic techniques, and more particularly to a method for assessing and displaying the three dimensional velocity magnitude of blood flow through an identified vessel using ultrasound.

2. Description of the Background Art

Diagnostic ultrasonic techniques in medicine are of growing importance, because they are non-invasive, non-ionizing, and of low cost as compared to other sensing and imaging methods. As a result, such techniques have been applied to assessing the integrity of the vascular system in a human body where it is necessary to determine the true magnitude of the flow velocity through the blood vessel. However, such a determination of the true three dimensional magnitude has not been possible using conventional ultrasound techniques because currently used strategies accurately measure velocity only in directions which are parallel to the beam; that is, radial or axial velocity, rather than transverse velocity.

As a result, various solutions for more accurate flow measurements have been proposed. For example, U.S. Pat. No. 4,265,126 issued to Papadofrangakis et al. on May 5, 1981, discloses using a cross-beam array configuration which is capable of resolving two orthogonal components of the velocity vector, the radial velocity component being resolved in the acoustic beamsteering direction and the transverse component being resolved at right angles to the beamsteering direction.

U.S. Pat. No. 5,000,184 issued to Bonnefous on Mar. 19, 1991, discloses measuring the axial and transverse components of the velocity in three dimensions using a mosaic of piezoelectric transducers.

U.S. Pat. No. 5,201,313 issued to Katakura on Apr. 13, 1993, discloses a flowmeter which utilizes an array of transducer elements to measure magnitude and velocity of flow, and further discloses a method of measuring the velocity at a right angle to an ultrasound beam by evaluating the flow rate in the transverse direction using the frequency spectrum of the detected signal.

U.S. Pat. No. 5,109,857 issued to Roundhill et al. on May 5, 1992, discloses that color flow doppler processors are not capable of measuring lateral or elevation vectors across the beam, and attempts to solve the problem by processing modulated signals returned from the test region to detect first and second ranges of data. The second range is compared to the first to determine positional displacement which indicates movement. From the movement data, velocity is determined.

U.S. Pat. No. 4,759,375 issued to Namekawa on Jul. 26, 1988, discloses use of ultrasonic pulse beams sent at different angles to determine radial velocity and tangential velocity. Tangential velocity is determined by obtaining first and second velocity distributions at different angles, and comparing the velocity distributions to obtain the vectorial velocity.

The foregoing approaches, however, are costly and difficult to use, thereby rendering conventional ultrasound techniques more practical. However, current systems are still based on using an estimate of the Doppler shift frequency to determine the axial velocity component, where the axial velocity is the velocity magnitude toward or away from the transducer. Therefore, such systems are unable to quantify the magnitude of any velocity component which crosses the transducer beam. As a result, these systems generally compensate for the absence of lateral information through one of two schemes: manipulation of the transducer to minimize the beam-vessel angle, thus maximizing the measured velocity component; or operator placement of a cursor in the direction of flow, based on the viewed image. In the latter case, the systems compute a two dimensional magnitude based on the direction of this cursor, but are unable to estimate motion in a direction into or out of the image.

Therefore, there is a need for a method for estimating the true three dimensional magnitude of blood velocity from ultrasound signals generated from conventional diagnostic equipment. The present invention satisfies that need, as well as others, and overcomes the deficiencies found in devices and techniques heretofore developed.

The foregoing patents reflect the state of the art of which the applicant is aware and are tendered with the view toward discharging applicant's acknowledged duty of candor in disclosing information which may be pertinent in the examination of this application. It is respectfully stipulated, however, that none of these patents teach or render obvious, singly or when considered in combination, applicant's claimed invention.

SUMMARY OF THE INVENTION

The present invention generally comprises a method for estimating the true three dimensional magnitude of blood velocity in a vessel. By way of example, and not of limitation, the method of the present invention includes the following core steps:

1. Subjecting a blood carrying vessel to beams of ultrasound imaging signals using a single transducer;
2. Estimating axial velocity using the speed of motion toward or away from the transducer;
3. Using the estimated axial velocity, identifying a region of laminar flow for which the lateral transit time limits the correlated signal interval; and
4. Estimating the lateral transit time of the blood flow across the lateral beam width in the region of laminar flow.

Next, an estimate of the true three dimensional velocity magnitude is determined using one of three further methods in accordance with the present invention.

In the first of these methods, the total distance across the lateral beam width traveled during the lateral transit time is estimated. The estimated three dimensional velocity magnitude is then determined from the ratio of the distance across the lateral beam width and the lateral transit time.

In the second of these methods, the beam to vessel angle is estimated. The estimated three dimensional velocity magnitude is then determined from the ratio of the axial velocity and the cosine of the beam to vessel angle.

In the third of these methods, the beam to vessel angle is also estimated. Next, the estimated lateral velocity is determined from the ratio of the lateral beam width and the lateral transit time. Finally, the estimated three dimensional velocity magnitude is determined from the ratio of the lateral velocity and the sine of the beam to vessel angle.

Once the three dimensional velocity magnitude is determined, it is displayed to the user numerically or graphically as an image. Where an image is displayed, it can be displayed as a two dimensional waveform as a function of time or as a color flow may where the velocity magnitude is represented by different colors and/or intensity of color.

An object of the invention is to accurately estimate the true three dimensional magnitude of fluid velocity through a vessel using conventional ultrasound devices.

Another object of the invention is to use ultrasound to locate tumors.

Another object of the invention is to use ultrasound to map vasculature.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

The following is a description of the preferred embodiments of the method for estimating the true three dimensional magnitude of blood velocity in accordance with the present invention. It will be appreciated, however, that the method of the present invention may vary as to specific steps and their sequence without departing from the basic concepts as disclosed herein.

Figure 1:
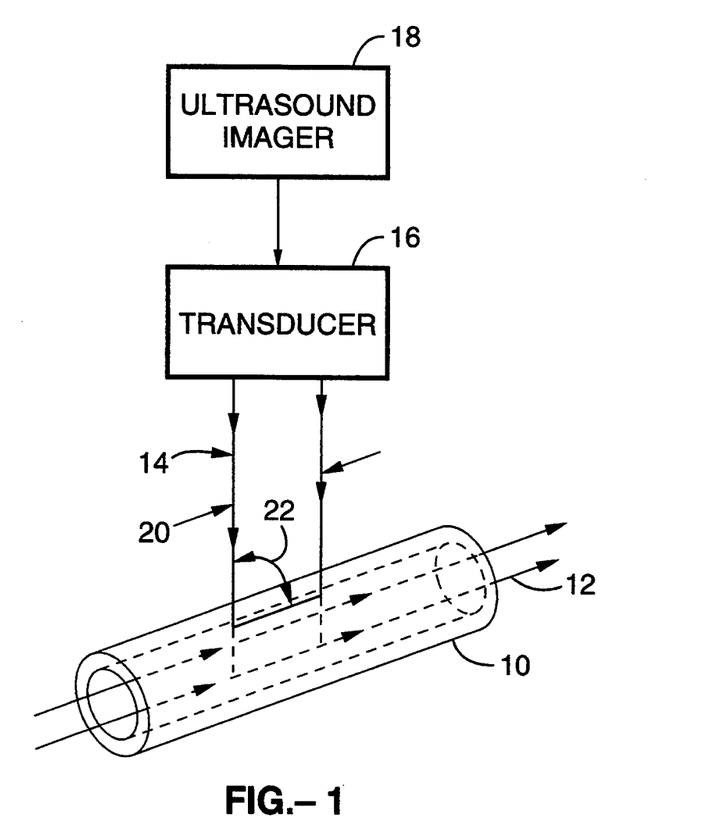
FIG. 1 is diagrammatic view of a vessel containing a flow of blood being subjected to ultrasound imaging signals.

Referring to FIG. 1, the first step in the method of the present invention is to subject an identified vessel 10 through which a fluid 12 is flowing to beams 14 ultrasonic imaging signals by positioning a transducer 16 from an ultrasound imaging apparatus 18 above the test subject containing the vessel 10. Ultrasonic signals are then transmitted and the reflections are received and processed in accordance with the present invention. While other applications of the method disclosed herein are within the scope of the invention, it is contemplated that the method of the present invention be applied to determining the three dimensional velocity magnitude of blood in a human body. Further, the imaging signals are produced from a conventional ultrasound diagnostic apparatus 18 or the like, and a single transducer 16 can be used. The imaging signals used comprise pulses of ultrasonic beams 14 transmitted by the transducer 16 and reflections of said pulsed beams received by said transducer, the beams having a lateral beam width 20 and a beam-vessel angle 22, the transmitted signals having a center frequency and acoustic propagation velocity, and the received signals having a complex envelope.

Figure 2:
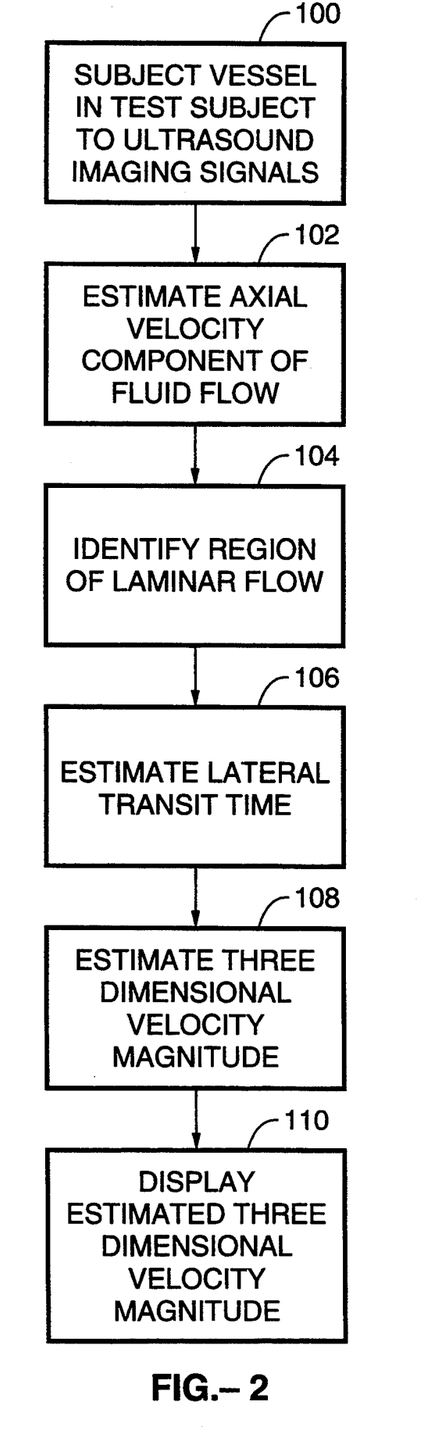
FIG. 2 is a flow chart showing typical steps employed in the method of the present invention.

Referring to FIG. 2, after the vessel is subjected to ultrasound imaging signals at step 100, at step 102 the axial velocity component of flow in a region of the vessel is estimated from the imaging signals using the speed of motion toward or away from the transducer. This can be accomplished by determining a likelihood of the axial velocity using a wideband maximum likelihood function, or by using conventional methods for estimating axial velocity. In accordance with the present invention, the likelihood function for a discrete velocity value v, corresponding to a two way travel time d, is preferably determined in according with the following equation (1):

$$l(v) \left| \sum_k \int_{-\infty}^{\infty} r'(t) s_0'^*(t - d - kT[1 + 2v/c]) \exp[j 2 w_c v t / c] dt \right|^2 \quad (1)$$

where
c = acoustic propagation velocity;
l(v) = likelihood of velocity v;
nl(v) = normalized likelihood of velocity v;
r'(t) = complex envelope of the received signal;
T = period of the transmitted pulse;
$s_0'(t)$ = deterministic portion of the received complex signal envelope;
v = axial velocity of the estimator;
$w_c$ = center frequency of the transmitted signal (radians/second);
d = two way travel time;
k = pulse train index; and
t = time.

Note also that the presence of v within the envelope matches the change in delay, and that the presence of v within the exponential matches the frequency shift of the red blood cells. Therefore, the likelihood involves the sum over the pulse train indexed by k, and the integral over the temporal axis, t. The integrand is the product of the complex envelope of the received signal, an estimate of the complex envelope of the received signal being denoted by $s_0'(\cdot)$ and the Doppler shift.

Next, at step 104, a region of laminar flow for which the lateral transit time of the blood flow across the lateral beam width limits the correlated signal interval is identified. The identification of an appropriate region is critical to the quality of the estimate, since the method of the present invention is not applicable to regions of turbulent flow. Identification of a small spatial region which contains laminar, nearly constant velocity flow is possible is accomplished by transmitting a wideband signal and tracking a group of cells for a short distance. Turbulent regions which contain velocity components with a variety of directional vectors, and regions of velocity spread near the vessel wall are thereby distinguished. Such regions do not contain a sufficiently narrow range of velocities to provide a meaningful estimate of the three dimensional velocity magnitude. The inability of previous techniques to distinguish such regions is a key factor in their failure to accurately estimate true three dimensional velocity.

Using the axial velocity previously estimated, this identification can be performed by one of the following ways:

1. Compare the Normalized Magnitude of the Likelihood Function to a Reference Standard This is the preferred approach which has been identified as providing the most accurate results. Using equation (1), the normalized likelihood function is given by:

$$nl(v) = \frac{\left|\sum_k \int_{-\infty}^{\infty} r'(t) s_0'^*(t - d - kT[1 + 2v/c]) \exp[j2w_c vt/c] dt\right|^2}{\sum_k \left|\int_{-\infty}^{\infty} r'(t) s_0'^*(t - d - kT[1 + 2v/c]) dt\right|^2} \quad (2)$$

Those skilled in the art will appreciate that if an equation other than equation (1) is used to estimate axial velocity, then the normalization function given in equation (2) will similarly be rewritten. The normalized reference standard used with this approach is approximately 0.65, with regions of laminar flow corresponding to values greater than the reference standard. The appropriate reference standard is easily determined based on the specific transducer used, beam frequency, and expected lateral beam width. If desired, the normalized likelihood magnitude can be used to create a visual map of colors which indicate a region of flow disturbance. The lines of maximum shear or flow disturbance have the minimum values of this ratio. Therefore, by plotting the log of the magnitudes and assigning colors to the log values, a map can be developed. For example, low values can be shown in blue whereas higher values indicating an undisturbed region can be shown in red. Color mapping is particularly suited where high velocity or disturbed flow exists. However, where velocity is low such as in tumorous regions, color mapping may not provide useful results.

2. Compare the Normalized Magnitude of the Signal Correlation to a Reference Standard This approach does not provide as accurate results as the approach set forth above, but can provide a reasonable indication of laminar flow. For purposes of this approach, the correlation of a pulse train of length N, between the signal arriving after a delay of time $t_o$ and the signal arriving after a delay $t_o + \tau + nT$, is studied as a function $\tau$ and n, and can be represented as:

$$C(t_0, t_0 + \tau; n) = \sum_{k=0}^{N-1} \int_{t_0}^{t_0 + W} r_k'(t + t_0) a(t + t_0) r_{k+n}'^*(t + t_0 + \tau) a(t + t_0 + \tau) dt \quad (3)$$

where n is the difference in pulse indices, $\tau$ is the time delay applied to the signal from an individual pulse, $r_k'(t)$ is the baseband return from the kth pulse, $a(t)$ represents the axial window of width W, and $t_o$ is a temporal offset where $0 < t_o < T$. The correlation is normalized by the averaged correlation at lag zero for each position. Here, the reference standard is approximately 0.75, with laminar flow being indicated at levels above the reference standard. Those skilled in the art will appreciate that other relationships could be used to determine correlation.

Note also that, in the case of the first two approaches set forth above, the correlation or the likelihood function is preferably evaluated at the maximum likelihood axial velocity, with an observation time which would correspond to the transit time for a 45 degree beam width.

3. Visually Inspect the High Resolution M-Mode Image

Using this approach, M-mode images of the fluid flow are viewed on a visual display. When viewing an M-mode image, regions of laminar flow are identified by a set of strong, continuous diagonal stripes on the display which indicate the shift in the rf signal carrier produced by the movement of the scattering medium. This identification can be performed using automated computer vision techniques.

4. Compare Adjacent Velocity Estimates

Under this approach, a region of laminar flow is identified by using adjacent velocity estimates in a region having a size which is on the order of the size of the same volume. In this case, if the difference between the velocity in two adjacent sample volumes exceeds the velocity difference which would cause the signal to decorrelate, the region is rejected. For a transducer having a center frequency of 7.5 MHz and with a short transmitted pulse, the velocity difference corresponding to the decorrelation threshold is on the order of 1 cm/s. By initially assuming an approximate beam to vessel angle of 45 degrees, the approximate criterion is:

$$2f_o/c(\Delta v)(bw/mv) < 1 \quad (4)$$

where, $f_o$ = the transducer center frequency;
$\Delta v$ = the velocity difference between two adjacent regions;
bw = the known transducer lateral beam width; and
mv = the mean velocity (the average of the estimated velocity in two adjacent regions).

Thus, if $\Delta v$ is computed from two adjacent regions and satisfies the above criterion, the angle estimate is deemed valid. It has been found that the error in the estimate can be expected to be less than approximately ten degrees.

Once a region of laminar flow is identified, the lateral transit time is then estimated at step 106 in order to determine the velocity in the direction perpendicular to the transducer beam in that region. This can be accomplished by estimating the temporal width of the signal correlation at a normalized magnitude using either equation (5) or equation (6) normalized by equation (7). The finite average autocorrelation is given by:

$$C(t_0, t_0 + \tau; n; \hat{k}) = \sum_{k=\hat{k}}^{\hat{k}+N-1} 1/(N) \int_{t_0}^{t_0 + W} r_k'(t + t_0) a(t + t_0) r_{k+n}'^*(t + t_0 + \tau) a(t + t_0 + \tau) dt \quad (5)$$

The correlogram is given by:

$$C(t_0, t_0 + \tau; n; \hat{k}) = \quad (6)$$

-continued $$MC(t_0, t_0; \hat{k}) = \sum_{k=\hat{k}}^{\hat{k}+N-|n|-1} 1/(N-|n|) \int_{t_0}^{t_0+W} r_k'(t + t_0)a(t+t_0)r_{k+n}'^*(t+t_0+\tau)a(t+t_0+\tau)dt \quad (5)$$

The correlation magnitude, computed for normalization of equations (5) and (6) at n=0 and ρ=0, is given by:

$$MC(t_0, t_0; \hat{k}) = \sum_{k=\hat{k}}^{\hat{k}+N-1} 1/(N) \int_{t_0}^{t_0+W} r_k'(t + t_0)a(t + t_0)r_k'^*(t + t_0)a(t + t_0)dt \quad (7)$$

where n is the difference in pulse indices, $\hat{k}$ is the starting pulse, $\tau$ is the time delay applied to the signal from an individual pulse, $r_k'(t)$ is the baseband return from the kth pulse, a(t) represents the axial window of width W, and $t_o$ is a temporal offset where $0 < t_o < T$. As indicated above, the experimental correlation of a pulse train of length N, between the signal arriving after a delay of time $t_o$ and the signal arriving after a delay $t_o + \tau + nT$, is studied as a function of $\tau$ and n. The value of n for which the normalized correlation slips below 0.5 or rises above 1.5 multiplied by the period T is the correlated signal interval.

Next, at step 108, the true three dimensional velocity magnitude is estimated. Once the three dimensional velocity magnitude is determined, it is displayed to the user numerically or graphically as an image at step 110. A numerical representation can be displayed on a video display, printer or the like; where an image is displayed, it can be displayed on a visual display device such as a video display, printer or the like, as a two dimensional waveform as a function of time or as a color flow map where the velocity magnitude is represented by different colors and/or intensity of color.

Figure 3:
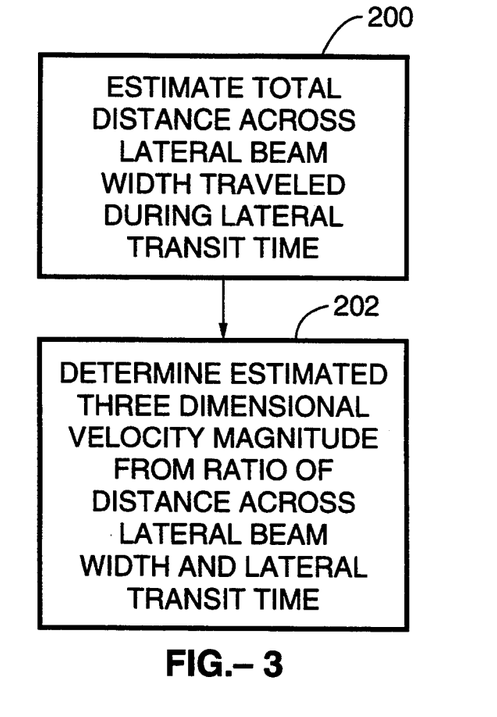
FIG. 3 is a flow chart showing typical steps employed for estimating the true three dimensional velocity magnitude in accordance with the method of FIG. 2.

The method of the present invention includes three methodologies for estimating the three dimensional velocity magnitude at step 108. The first of these methods can be seen with reference to FIG. 3. At step 200, the total distance across the lateral beam width traveled during the lateral transit time for the unknown beam to vessel angle is estimated. First, the axial distance traveled is determined by multiplying the axial velocity and the lateral transit time. The three dimensional distance traveled during the lateral transit time is equal to the vector sum of the lateral beam width and the axial distance travelled. Therefore, for an unknown angle, the total distance traveled at a depth of interest can be estimated as:

estimated distance = vector sum [lateral beam width + (axial velocity × lateral transit time)]   (8)

The lateral transit time is equal to the true three dimensional velocity magnitude multiplied by the distance across the beam at the beam to vessel angle. Therefore, the final step 202 is to compute the ratio of the estimated distance across the beam from the vector sum as in equation (8) and the lateral transit time. An estimate of the true three dimensional velocity magnitude is represented by that ratio.

Figure 4:
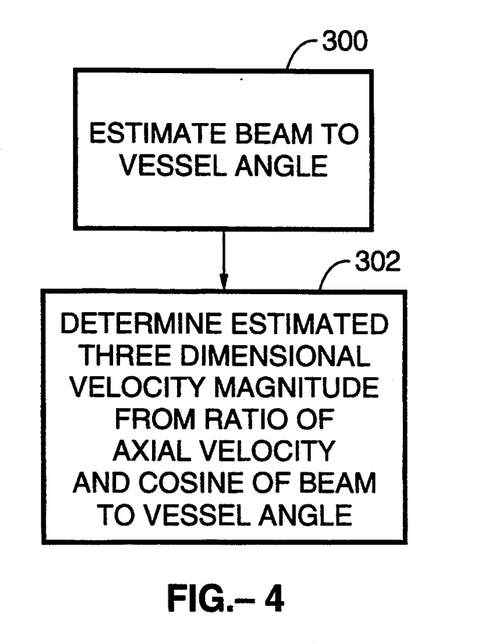
FIG. 4 is a flow chart showing an alternative embodiment of the method of FIG. 3.

Referring now to FIG. 1 and FIG. 4, the true three dimensional velocity magnitude can also be estimated from the beam to vessel angle 22. The beam to vessel angle is estimated at step 300 from the geometrical relationship of the lateral beam width, the axial distance travelled, and the total distance travelled. The angle can be estimated as the (i) inverse cosine of the ratio of the axial distance and the total distance, (ii) inverse sine of the ration of the lateral beam width and the total distance, or (iii) inverse tangent of the ratio of the axial distance and the lateral beam width. At step 302, the estimated true three dimensional velocity magnitude is determined from the ratio of the axial velocity and the cosine of the beam to vessel angle.

Figure 5:
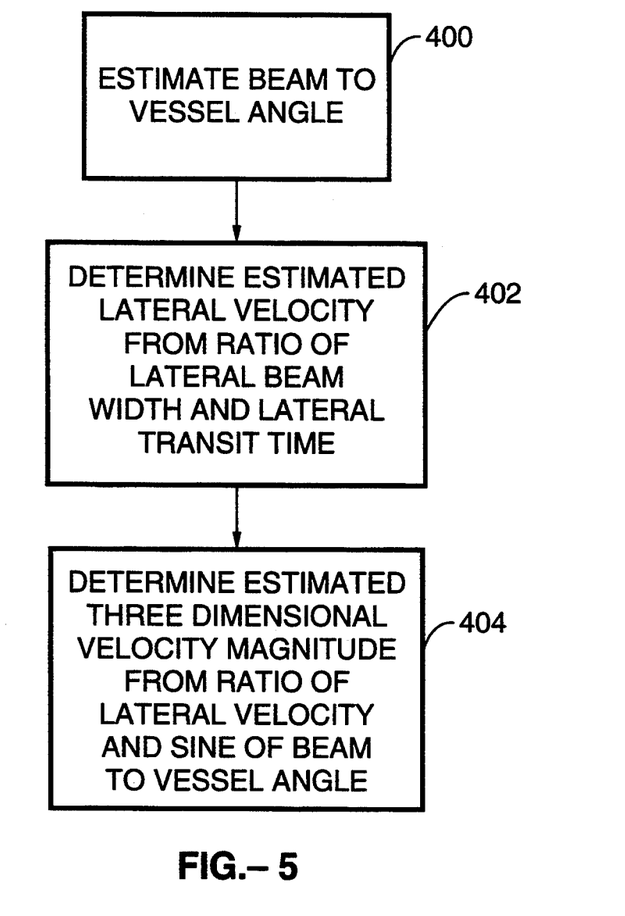
FIG. 5 is a flow chart showing an alternative embodiment of the method of FIG. 4.

FIG. 5 shows an alternative methodology to that shown in FIG. 4. At step 400, the beam to vessel angle is estimated as before. Next, at step 402 the estimated lateral velocity is determined from the ratio of the lateral beam width and the lateral transit time. Finally, at step 404 the estimated true three dimensional velocity magnitude is determined from the ratio of the lateral velocity and the sine of the beam to vessel angle.

Using the foregoing method, we have successfully estimated the true three dimensional velocity magnitude on a vessel phantom for known angles of 45, 60 and 85 degrees as shown in Tables 1 through 3.

TABLE 1

| 45 Degree Beam Vessel Angle; 0.17 cm Vessel Radius | | | | | |
|---|---|---|---|---|---|
| Flow Rate (mLs) | 0.05 | 0.1 | 0.5 | 1 | 2 |
| Predicted peak axial velocity (cm/s) | 0.778 | 1.56 | 7.78 | 15.6 | 31.15 |
| Estimated peak axial velocity (cm/s) | 0.9 | 1.94 | 8.25 | 16.5 | 33 |
| Predicted peak lateral velocity (cm/s) | 0.778 | 1.56 | 7.78 | 15.6 | 31.15 |
| Predicted transit time (ms) | 83.5 | 41.8 | 8.35 | 4.18 | 2.1 |
| Limit on the axial velocity gradient (cm/s) | 0.061 | 0.123 | 0.61 | 1.23 | 2.46 |
| Predicted transit time (pulses) | 669.1 | 334.5 | 66.9 | 33.4 | 16.7 |
| Estimated correlated signal interval (pulses) across vessel | >500 | 90–250 | 25–70 | 30–50 | 3–8 |
| Transit time estimate (pulses) for vessel center | 650 | 220 | 54 | 30 | 8 |
| Estimated angle (degrees) | 41.7 | 50.66 | 49.45 | 47.3 | 63.12 |
| Predicted peak 3D velocity magnitude (cm/s) | 1.10 | 2.20 | 11.01 | 22.03 | 44.06 |
| Estimated peak 3D velocity magnitude (cm/s) | 1.20 | 3.06 | 12.6 | 23.6 | 72 |

TABLE 2

| 60 Degree Beam Vessel Angle; 0.1 cm Vessel Radius | | | | | |
|---|---|---|---|---|---|
| Flow Rate (mL/s) | 0.05 | 0.1 | 0.5 | 1 | 2 |
| Predicted peak axial velocity (cm/s) | 1.59 | 3.18 | 15.8 | 31.8 | 63.6 |
| Estimated peak axial velocity (cm/s) | 1.69 | 4.0 | 17.0 | 31.5 | 57 |

TABLE 2-continued

| 60 Degree Beam Vessel Angle; 0.1 cm Vessel Radius | | | | | |
|---|---|---|---|---|---|
| Flow Rate (mL/s) | 0.05 | 0.1 | 0.5 | 1 | 2 |
| Predicted peak lateral velocity (cm/s) | 2.36 | 5.51 | 27.6 | 55.1 | 110.2 |
| Predicted transit time (ms) | 22.5 | 11.8 | 2.36 | 1.18 | 0.59 |
| Limit on the axial velocity gradient (cm/s) | 0.23 | 0.45 | 2.28 | 4.56 | 9.12 |
| Predicted transit time (pulses) | 189 | 94.3 | 18.8 | 9.43 | 4.72 |
| Estimated correlated signal interval (pulses) across vessel | 100–250 | 50–105 | 12 | 5 | 3–4 |
| Transit Time Estimate (pulses) for vessel center | 160 | 52 | 12 | 5 | 3 |
| Estimated angle (degrees) | 62.56 | 68.23 | 68.6 | 75 | 71.8 |
| Predicted peak 3D velocity magnitude (cm/s) | 3.18 | 6.37 | 31.8 | 63.7 | 127.32 |
| Estimated peak 3D velocity magnitude (cm/s) | 3.66 | 10.78 | 46.61 | 124 | 182.7 |

TABLE 3

| 85 Degree Beam Vessel Angle; 0.1 cm Vessel Radius | | | | | |
|---|---|---|---|---|---|
| Flow Rate (mL/s) | 0.05 | 0.1 | 0.5 | 1 | 2 |
| Predicted peak axial velocity (cm/s) | 0.277 | 0.554 | 2.77 | 5.54 | 11.08 |
| Estimated peak axial velocity (cm/s) | 0.5 | 0.635 | 2.7 | 5 | 15 |
| Predicted peak lateral velocity (cm/s) | 3.17 | 6.34 | 31.7 | 63.4 | 126.8 |
| Predicted transit time (ms) | 20.5 | 10.25 | 2.05 | 1.03 | 0.51 |
| Limit on the axial velocity gradient (cm/s) | 0.25 | 0.50 | 2.50 | 5.01 | 10.02 |
| Predicted transit time (pulses) | 164.3 | 82.12 | 16.43 | 8.2 | 4.1 |
| Estimated correlated signal interval (pulses) across vessel | 125–250 | 80–150 | 12–18 | 9–10 | 3–4 |
| Transit time estimate (pulses) for vessel center | 125 | 85 | 14 | 9 | 3 |
| Estimated angle (degrees) | 84.44 | 82.83 | 86.79 | 85.7 | 84.27 |
| Predicted peak 3D velocity magnitude (cm/s) | 3.18 | 6.37 | 31.8 | 63.7 | 127.32 |
| Estimated peak 3D velocity magnitude (cm/s) | 5.15 | 7.53 | 42.86 | 66.68 | 150.23 |

Results which are clearly skewed are highlighted in Table 1 for a 2.0 mL/s flow rate and in Table 2 for a 1.0 mL/s flow rate as double bordered boxes. Examination of the axial velocity profile for those samples showed that the change in axial velocity between the volumes that approximate the size of the sample volume exceeded the threshold used, which is listed in the tables as the limit on the axial velocity gradient. Also, the results in Table 1 and 2 show an overestimation of the beam to vessel angle which may be due to a error in the transit time from the signal correlation, using the normalized correlation threshold of 0.5. A second possible source of error is the effect of axial velocity spread. We have also successfully conducted an in-vivo experiment in which we acquired data from a cephalic vein and inferior ulnar collateral artery at an angle of 45 degrees. In those instances, the error was less than 5 degrees.

An additional application of the method of using an estimate of the three dimensional correlation or normalized likelihood is in the detection of flow at an angle of approximately 90 degrees. At such an angle, both the magnitude of the correlation and normalized likelihood can be used in addition to the shift of the peak of the correlation, and the maximum likelihood velocity. The correlation is computed at lags of approximately 2.5, 5.0 and 10.0 ms. A change in the normalize likelihood or normalized correlation which corresponds to a 50 percent increase or decrease over the 10 ms interval indicates flow. This change is then logically "or"ed with a detection of flow from any other method. This method will augment flow detection in the new modalities known as power or intensity "Doppler" imaging.

Accordingly, it will be seen that this invention provides for a simple, efficient, and accurate estimate of the true three dimensional velocity magnitude of blood flow, without the need for using multiple transducer arrays, or other costly and complex equipment. A single transducer can be used in conjunction with a conventional ultrasound diagnostic apparatus or the like, and accurate determinations can be made. A patient can then be diagnosed and/or treated in accordance with the blood flow information obtained in accordance with the present invention.

Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A method for assessing three dimensional magnitude of velocity of a fluid flowing through an identified vessel of a test subject using ultrasound imaging, comprising the steps of:

(a) subjecting a fluid flowing through an identified vessel in a test subject to ultrasound imaging signals, said fluid flow having a three dimensional velocity magnitude, said imaging signals comprising pulses of ultrasonic beams transmitted by a transducer and reflections of said pulsed beams received by said transducer, said beams having a lateral beam width, said beams having a beam to vessel angle;

(b) estimating axial velocity of said fluid from said imaging signals;

(c) identifying a region of laminar flow of said fluid in said vessel using said axial velocity;

(d) estimating lateral transit time of said fluid across said lateral beam width in said region of laminar flow; and (e) estimating said three dimensional velocity magnitude for said fluid flow using said lateral transit time.

2. A method as recited in claim 1, further comprising the step of displaying said three dimensional velocity magnitude on a visual display device.

3. A method as recited in claim 1, wherein said step of estimating said three dimensional velocity magnitude for said fluid flow using said lateral transit time comprises the steps of:
   (a) estimating the total distance across said lateral beam width travelled during said lateral transit time; and
   (b) determining said three dimensional velocity magnitude as a ratio of said total distance across said lateral beam width and said lateral transit time.

4. A method as recited in claim 1, wherein said step of estimating said three dimensional velocity magnitude for said fluid flow using said lateral transit time comprises the steps of:
   (a) estimating said beam to vessel angle using said lateral transit time; and
   (b) determining said three dimensional velocity magnitude as a ratio of said axial velocity and the cosine of said beam to vessel angle.

5. A method as recited in claim 1, wherein said step of estimating said three dimensional velocity magnitude for said fluid flow using said lateral transit time comprises the steps of:
   (a) estimating said beam to vessel angle using said lateral transit time;
   (b) estimating lateral velocity of said fluid as a ratio of said lateral beam width and said lateral transit time; and
   (c) determining said three dimensional velocity magnitude as a ratio of said lateral velocity and the sine of said beam to vessel angle.

6. A method as recited in claim 1, wherein said axial velocity is estimated using a wideband maximum likelihood function and wherein said step of identifying a region of laminar flow includes the steps of:
   (a) normalizing the likelihood of said axial velocity; and
   (b) comparing said normalized likelihood of axial velocity to a reference standard.

7. A method as recited in claim 1, wherein said step of identifying a region of laminar flow includes the steps of:
   (a) determining a normalized magnitude of signal correlation; and
   (b) comparing said normalized magnitude of signal correlation to a reference standard.

8. A method as recited in claim 1, wherein said step of identifying a region of laminar flow includes the step of viewing an M-mode image on a visual display and identifying images having continuous diagonal stripes.

9. A method as recited in claim 1, wherein said step of identifying a region of laminar flow includes the steps of:
   (a) determining a difference in fluid velocity between adjacent fluid volumes; and
   (b) comparing said velocity difference to a decorrelation threshold.

10. A method for using ultrasound imaging to assess and display a three dimensional magnitude of blood velocity in an identified vessel of a test subject, comprising the steps of:
    (a) subjecting a fluid flowing through an identified vessel in a test subject to ultrasound imaging signals, said fluid flow having a three dimensional velocity magnitude, said imaging signals comprising pulses of ultrasonic beams transmitted by a transducer and reflections of said pulsed beams received by said transducer, said beams having a lateral beam width, said beams having a beam to vessel angle;
    (b) estimating axial velocity of said fluid from said imaging signals;
    (c) identifying a region of laminar flow of said fluid in said vessel using said axial velocity;
    (d) estimating lateral transit time of said fluid across said lateral beam width in said region of laminar flow;
    (e) estimating said three dimensional velocity magnitude for said fluid flow using said lateral transit time; and
    (f) displaying said three dimensional velocity magnitude on a visual display device.

11. A method as recited in claim 10, wherein said step of estimating said three dimensional velocity magnitude for said fluid flow using said lateral transit time comprises the steps of:
    (a) estimating the total distance across said lateral beam width traveled during said lateral transit time; and
    (b) determining said three dimensional velocity magnitude as a ratio of said total distance across said lateral beam width and said lateral transit time.

12. A method as recited in claim 10, wherein said step of estimating said three dimensional velocity magnitude for said fluid flow using said lateral transit time comprises the steps of:
    (a) estimating said beam to vessel angle using said lateral transit time; and
    (b) determining said three dimensional velocity magnitude as a ratio of said axial velocity and the cosine of said beam to vessel angle.

13. A method as recited in claim 10, wherein said step of estimating said three dimensional velocity magnitude for said fluid flow using said lateral transit time comprises the steps of:
    (a) estimating said beam to vessel angle using said lateral transit time; and
    (b) estimating lateral velocity of said fluid as a ratio of said lateral beam width and said lateral transit time; and
    (c) determining said three dimensional velocity magnitude as a ratio of said lateral velocity and the sine of said beam to vessel angle.

14. A method as recited in claims 10, 11, 12 or 13, wherein said axial velocity is estimated using a wideband maximum likelihood function and wherein said step of identifying a region of laminar flow includes the steps of:
    (a) normalizing the likelihood of said axial velocity; and
    (b) comparing said normalized likelihood of axial velocity to a reference standard.

15. A method as recited in claims 10, 11, 12 or 13 wherein said step of identifying a region of laminar flow includes the steps of:
    (a) determining a normalized magnitude of signal correlation; and
    (b) comparing said normalized magnitude of signal correlation to a reference standard.

16. A method as recited in claims 10, 11, 12 or 13, wherein said step of identifying a region of laminar flow includes the step of viewing an M-mode image on a visual display and identifying images having continuous diagonal stripes.

17. A method as recited in claims 10, 11, 12 or 13, wherein said step of identifying a region of laminar flow includes the steps of:
   (a) determining a difference in fluid velocity between adjacent fluid volumes; and
   (b) comparing said velocity difference to a decorrelation threshold.

18. A method for estimating true three dimensional magnitude of fluid flow in an identified vessel of a test subject wherein said vessel is subjected to ultrasound imaging signals at an unknown angle, comprising the steps of:
   (a) subjecting a fluid flowing through an identified vessel in a test subject to ultrasound imaging signals, said fluid flow having a three dimensional velocity magnitude, said imaging signals comprising pulses of ultrasonic beams transmitted by a transducer and reflections of said pulsed beams received by said transducer, said beams having a lateral beam width, said beams having a beam to vessel angle, said transmitted signals having a center frequency, said transmitted signals having an acoustic propagation velocity, said received signals having a complex envelope;
   (b) estimating axial velocity of said fluid from said imaging signals by determining a likelihood of said axial velocity according to $$l(v) \propto \left| \sum_k \int_{-\infty}^{\infty} r'(t) s_0'^*(t - d - kT[1 + 2v/c]) \exp[j2w_c vt/c] dt \right|^2$$

where:
c = acoustic propagation velocity;
l(v) = likelihood of velocity v;
r'(t) = complex envelope of the received signal;
T = period of the transmitted pulse;
$s_0'(t)$ = deterministic portion of the received complex signal envelope;
v = axial velocity;
$w_c$ = center frequency of the transmitted signal (radians/second);
d = two way travel time;
k = pulse train index; and
t = time;

(c) identifying a region of laminar flow of said fluid in said vessel using said axial velocity;
   (d) estimating lateral transit time of said fluid across said lateral beam width in said region of laminar flow; and
   (e) estimating said three dimensional velocity magnitude for said fluid flow using said lateral transit time.

19. A method as recited in claim 18, wherein said axial velocity is estimated using a wideband maximum likelihood function and wherein said step of identifying a region of laminar flow includes the steps of:
   (a) normalizing the likelihood of said axial velocity; and
   (b) comparing said normalized likelihood of axial velocity to a reference standard.

20. A method as recited in claim 19, wherein said likelihood of axial velocity is normalized according to $$nl(v) = \frac{\left| \sum_k \int_{-\infty}^{\infty} r'(t) s_0'^*(t - d - kT[1 + 2v/c]) \exp[j2w_c vt/c] dt \right|^2}{\sum_k \left| \int_{-\infty}^{\infty} r'(t) s_0'^*(t - d - kT[1 + 2v/c]) dt \right|^2}$$

where:
c = acoustic propagation velocity;
l(v) = likelihood of velocity v;
nl(v) = normalized likelihood of velocity v;
r'(t) = complex envelope of the received signal;
T = period of the transmitted pulse;
$s_0'(t)$ = deterministic portion of the received complex signal envelope;
v = axial velocity of the estimator;
$w_c$ = center frequency of the transmitted signal (radians/second);
d = two way travel time;
k = pulse train index; and
t = time.

21. A method as recited in claim 18, wherein said step of identifying a region of laminar flow includes the steps of:
   (a) determining a normalized magnitude of signal correlation; and
   (b) comparing said normalized magnitude of signal correlation to a reference standard.

22. A method as recited in claim 21, wherein said normalized magnitude of signal correlation C(t,n) is determined according to $$C(t_0, t_0 + \tau; n) = \sum_{k=0}^{N-1} \int_{t_0}^{t_0 + W} r_k'(t + t_0) a(t + t_0) r_{k+n}'^*(t + t_0 + \tau) a(t + t_0 + \tau) dt$$

for a pulse train of length N, between a signal arriving after a delay of time $t_0$ and a signal arriving after a delay $t_0 + \tau + nT$, where T is the period of the transmitted pulse, n is the difference in pulse indices, $\tau$ is the time delay applied to the signal from an individual pulse, $r_k'(t)$ is a baseband return from the kth pulse, a(t) represents an axial window of width W, $t_0$ is a temporal offset where $0 < t_0 < T$, and the correlation is normalized by the averaged correlation at lag zero for each position.

23. A method as recited in claim 18, wherein said step of identifying a region of laminar flow includes the steps of viewing an M-mode image on a visual display and identifying images having continuous diagonal stripes.

24. A method as recited in claim 18, wherein said step of identifying a region of laminar flow includes the steps of:
   (a) determining a difference in fluid velocity between adjacent fluid sample volumes; and
   (b) comparing said velocity to a decorrelation threshold.

25. A method as recited in claim 18, wherein said step of estimating said three dimensional velocity magnitude for said fluid flow using said lateral transit time comprises the steps of:

(a) estimating the total distance across said lateral beam width travelled during said lateral transit time; and (b) determining said three dimensional velocity magnitude as a ratio of said total distance across said lateral beam width and said lateral transit time.

26. A method as recited in claim 18, wherein said step of estimating said three dimensional velocity magnitude for said fluid flow using said lateral transit time comprises the steps of:

(a) estimating said beam to vessel angle using said lateral transit time; and (b) determining said three dimensional velocity magnitude as a ratio of said axial velocity and the cosine of said beam to vessel angle.

27. A method as recited in claim 18, wherein said step of estimating said three dimensional velocity magnitude for said fluid flow using said lateral transit time comprises the steps of:

(a) estimating said beam to vessel angle using said lateral transit time; and (b) estimating lateral velocity of said fluid as a ratio of said lateral beam width and said lateral transit time; and (c) determining said three dimensional velocity magnitude as a ratio of said lateral velocity and the sine of said beam to vessel angle.

* * * * *